US00PP30279P2

(12) United States Plant Patent
Hansen

(10) Patent No.: US PP30,279 P2
(45) Date of Patent: Mar. 5, 2019

(54) **X *MANGAVE* PLANT NAMED 'BAD HAIR DAY'**

(50) Latin Name: ***X Mangave* hybrid**
Varietal Denomination: Bad Hair Day

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,140

(22) Filed: Feb. 9, 2018

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and unique X *Mangave* plant named 'Bad Hair Day' characterized by numerous, long, narrow, horizontal leaves with irregular, dark-burgundy spotting covering large portions of leaves when grown in high ultraviolet light exposure. Leaf margin has minimal marginal spines and apical spines are flexible teeth. Growth rate is moderate. 'Bad Hair Day' is suitable for the garden or as a potted plant in the garden or home.

1 Drawing Sheet

Botanical classification: X *Mangave* hybrid; *Manfreda* times *Agave*.

Variety denomination: 'Bad Hair Day'.

BACKGROUND OF THE INVENTION

The present invention relates to the new and distinct X *Mangave* hybrid plant, X *Mangave* 'Bad Hair Day' hybridized by the inventor at a wholesale perennial nursery in Zeeland, Mich., USA as cross between an unnamed proprietary selection of *Manfreda maculosa* (not patented) as the female or seed parent times an unnamed proprietary selection of *Agave geminiflora* (not patented) as the male or pollen parent. The cross was performed Mar. 14, 2011 and seeds were later harvested and sown on Aug. 8, 2011. Through trials at the same nursery the plant was assigned the breeder code XMANG-11-01-08. The new plant has been successfully asexually propagated initially by sterile shoot-tip tissue culture at the same nursery in Zeeland, Mich. For those skilled in the art this method of asexual propagation system has been found to produce stable and identical plants that maintain all the unique characteristics of the original plant.

No plants of X *Mangave* 'Bad Hair Day' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Bad Hair Day' differs from its parents as well as all other *Manfreda, Agave* and X *Mangave* known to the applicant. The most similar known cultivar is X *Mangave* 'Man of Steel' U.S. Plant Pat. No. 29,196. Compared with the male parent, the new plant has slightly broader and thinner leaves with flatter habit. The female parent has broader more concavo-convex leaves with more outright to horizontal habit and the leaf color is chartreuse with larger burgundy spotting than the new plant, the leaf margins are filiferous and more fibrous. 'Man of Steel' has a more glaucous silvery-green leaves with less burgundy spotting and more outright leaf attitude.

'Bad Hair Day' is unique from all of the above cultivars and all *Agave*, X *Mangave* and *Manfreda* known to the inventor by the following combined traits:

1. Numerous, long, narrow, gracefully arching foliage;
2. Foliage develops irregular, dark-burgundy spotting especially in high ultraviolet light exposure;
3. Leaf margins have minimal marginal spines and terminal spines are flexible through drying;
4. Moderate growth rate.

BRIEF DESCRIPTION OF THE DRAWINGS

The photographs of x *Mangave* 'Bad Hair Day' demonstrate the overall appearance of the new plant including the unique traits as a five-year-old plant initially grown in a container in a greenhouse in Zeeland, Mich. with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
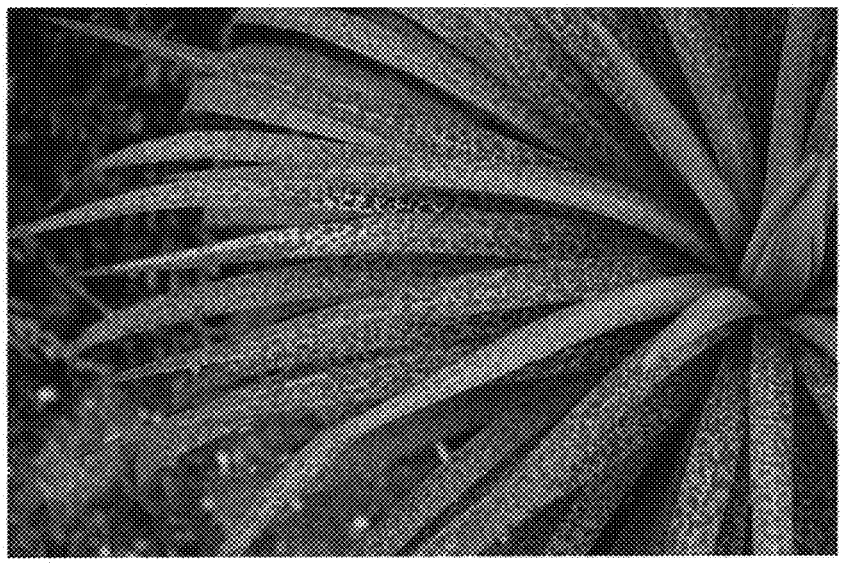
FIG. 1 shows a close-up of the foliage of the new plant with heavy burgundy spotting and greyed-purple blush on the older foliage and lighter green emerging foliage.
Figure 2:
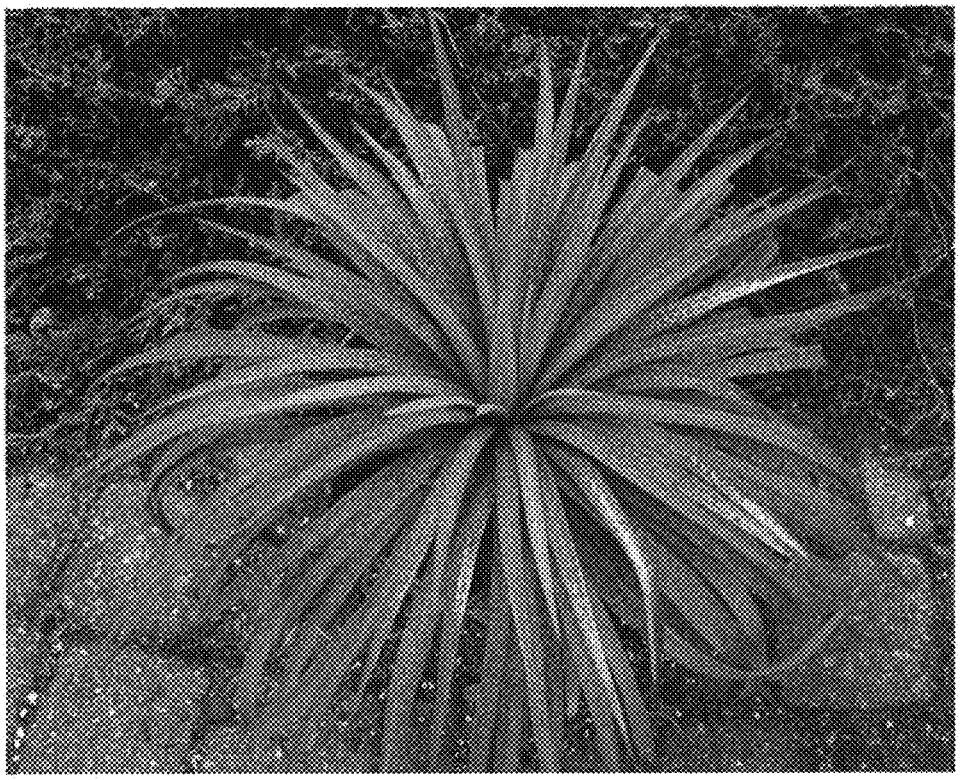
FIG. 2 shows the habit of the new plant grown in a container.

The following descriptions and color references are based on the 2015 edition of The Royal Horticultural Society Colour Chart except where common dictionary terms are used. The new plant, X *Mangave* 'Bad Hair Day', has not been observed under all possible environments. The phenotype may vary slightly with different environmental conditions, such as temperature, light, fertility, moisture and maturity levels, but without any change in the genotype. The following observations and size descriptions are of a five-year old plant in a commercial wholesale greenhouse in Zeeland, Mich. and also with a season of outdoor growth receiving supplemental water and fertilizer as needed.

Parentage: An unnamed proprietary selection of *Manfreda maculosa* (not patented) as the female or seed parent; an unnamed propriety selection of *Agave geminiflora* (not patented) as the male or pollen parent;

Propagation: Division of side shoots and sterile shoot-tip tissue culture;

Time to initiate roots from tissue culture: About three weeks;

Growth rate: Moderate;

Crop time: About 16 to 20 weeks to finish in a 3.8 liter container from a 35 mm tissue culture growing at about 21° C.;

Rooting habit: Fleshy, lightly branching, with roots up to 20 cm long;

Root color: Nearest RHS 158C;

Plant shape and habit: Succulent herbaceous perennial with basal rosettes of about 320 leaves per plant, radially emerging from central rhizome extending below the base of the plant and drooping in maturity when grown in containers, producing a radially-symmetrical, rounded mound;

Plant size: Foliage height about 10.0 cm tall from soil line to the top of emerging leaves and about 30.0 cm wide at the widest point slightly below soil line in container and drooping to about 20.0 cm below soil line when grown in elevated containers;

Foliage description: Gladiate to linear; simple; margins finely dentate; apex narrowly acute; base truncate, sessile, clasping; flattened; bi-laterally symmetrical; with dense, irregular, burgundy spotting from 0.5 mm to about 3.0 mm across, more pronounced on adaxial surface; glaucous both surfaces;

Leaf size: To about 29.0 cm long, about 9.0 cm wide at base and about 2.0 mm thick; average about 27.0 cm long, about 8.0 cm wide and about 2.0 mm thick;

Foliage fragrance: None observed;

Leaf blade color:

*Adaxial* (*mature*).—In low ultraviolet light between RHS 139B and RHS 138B with spots nearest RHS 138A; in high ultraviolet light exposure nearest RHS 146D with blush of nearest RHS N186C and spots of a blend between RHS N186C and RHS N187A becoming more dense and numerous with greater ultraviolet light exposure; Abaxial (mature): in low ultraviolet light exposure blend between RHS 138A and RHS 138B with spots about 1.0 to 2.0 mm across of blend between RHS 139A and RHS 139B; in high ultraviolet light exposure nearest RHS 138B with spots becoming blushed with a blend nearest RHS N186C and RHS N187C.

*Adaxial* (*young*).—Nearest RHS 138C maculate with nearest RHS 138B.

*Abaxial* (*young*).—Nearest RHS 138C and blotched with between RHS 138B and RHS 138A.

*Teeth* (*marginal*).—Small, about 0.5 mm long and about 4.0 mm apart; color nearest RHS 176B.

Apical spine: Flexible, frequently drying in older leaves, about 4.0 mm long; color nearest RHS 177B;

Petiole: Sessile;

Veins: Parallel; not distinct abaxial or adaxial;

Flower description: Not yet observed;

Fruit and seed: Not yet observed;

Disease resistance: X *Mangave* 'Bad Hair Day' has not been observed to be resistant to diseases beyond that which is normal for X *Mangave, Agave* or *Manfreda*. The plant is xeromorphic and survives well with minimal water once established. The new plant is hardy at least from USDA zone 7b to 10. Full extent of winter hardiness has not been tested.

It is claimed:

1. A new and distinct cultivar of ornamental X *Mangave* plant named 'Bad Hair Day' as herein described and illustrated.

* * * * *